(12) United States Patent
Torabi et al.

(10) Patent No.: US 12,064,184 B2
(45) Date of Patent: Aug. 20, 2024

(54) SYSTEM AND METHOD FOR INSTALLING BONE HARDWARE OUTSIDE AN END-EFFECTORS TOOL PATH

(71) Applicant: THINK SURGICAL, INC., Fremont, CA (US)

(72) Inventors: Meysam Torabi, Fremont, CA (US); Rose Cipriano, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 1115 days.

(21) Appl. No.: 16/763,280

(22) PCT Filed: Nov. 30, 2018

(86) PCT No.: PCT/US2018/063296
§ 371 (c)(1),
(2) Date: May 12, 2020

(87) PCT Pub. No.: WO2019/108925
PCT Pub. Date: Jun. 6, 2019

(65) Prior Publication Data
US 2020/0281656 A1  Sep. 10, 2020

Related U.S. Application Data (60) Provisional application No. 62/636,521, filed on Feb. 28, 2018, provisional application No. 62/593,020, filed on Nov. 30, 2017.

(51) Int. Cl.
*A61B 34/10* (2016.01)
*A61B 17/00* (2006.01)
(Continued)

(52) U.S. Cl.
CPC .......... *A61B 34/10* (2016.02); *A61B 17/8897* (2013.01); *A61B 34/20* (2016.02);
(Continued)

(58) Field of Classification Search
CPC ......... A61B 34/10; A61B 34/20; A61B 34/25; A61B 34/37; A61B 90/39; A61B 17/8897;
(Continued)

(56) References Cited

U.S. PATENT DOCUMENTS

| | | | | |
|---|---|---|---|---|
| 5,086,401 A | * | 2/1992 | Glassman | A61F 2/46 606/88 |
| 6,033,415 A | * | 3/2000 | Mittelstadt | A61B 90/36 600/425 |

(Continued)

FOREIGN PATENT DOCUMENTS

| | | |
|---|---|---|
| WO | 2002039917 A1 | 5/2002 |
| WO | 2017151751 A1 | 9/2017 |

OTHER PUBLICATIONS

Int'l. Search Report for PCT/US2018/063296, dated Mar. 26, 2019.
Supplemental European Search Report issued in corresponding EP Patent Appln. No. EP18882457, dated Jul. 1, 2021.

*Primary Examiner* — Kevin T Truong
*Assistant Examiner* — Diana Jones
(74) *Attorney, Agent, or Firm* — MaxGoLaw PLLC (57) ABSTRACT

A system and method are described herein for installing hardware in a bone outside an end-effector's tool path prior to modifying the bone. The method includes the installation of a first piece of hardware in the bone. The bone and a cut volume to be created in the bone is registered to a computer-assist device. A processor calculates whether the hardware is within the cut volume based on the geometry and POSE of the hardware relative to the POSE of the cut volume. A user is notified if the hardware is at or inside the cut volume based on the calculation. If so, a second piece of hardware is installed in the bone and the calculation is repeated to determine if the second piece of hardware is at or inside the cut volume. The surgical procedure may commence when an (Continued)

installed piece of hardware is installed outside the cut volume.

15 Claims, 8 Drawing Sheets

(51) Int. Cl.
| | |
|---|---|
| *A61B 17/88* | (2006.01) |
| *A61B 34/00* | (2016.01) |
| *A61B 34/20* | (2016.01) |
| *A61B 34/37* | (2016.01) |
| *A61B 90/00* | (2016.01) |

(52) U.S. Cl.
CPC .............. *A61B 34/25* (2016.02); *A61B 34/37* (2016.02); *A61B 90/39* (2016.02); *A61B 2017/00115* (2013.01); *A61B 2034/104* (2016.02); *A61B 2034/105* (2016.02); *A61B 2034/2051* (2016.02); *A61B 2034/2055* (2016.02); *A61B 2034/2059* (2016.02); *A61B 2034/2068* (2016.02); *A61B 2034/252* (2016.02); *A61B 2090/3916* (2016.02); *A61B 2090/3945* (2016.02); *A61B 2090/3983* (2016.02)

(58) Field of Classification Search
CPC ........ A61B 2034/104; A61B 2034/105; A61B 2034/2051; A61B 2034/2055; A61B 2034/2059; A61B 2034/2068; A61B 2034/252; A61B 2090/3916; A61B 2090/3945; A61B 2090/3983; A61B 2017/00115

See application file for complete search history.

(56) References Cited

U.S. PATENT DOCUMENTS

| | | | |
|---|---|---|---|
| 6,430,434 B1 * | 8/2002 | Mittelstadt ........... | A61B 17/175 606/130 |
| 6,711,432 B1 | 3/2004 | Krause et al. | |
| 7,043,961 B2 * | 5/2006 | Pandey ................ | A61B 34/20 73/1.79 |
| 7,206,626 B2 * | 4/2007 | Quaid, III .......... | A61B 17/1703 600/407 |
| 8,876,830 B2 * | 11/2014 | Hodorek ............. | A61B 17/155 606/88 |
| 8,961,536 B2 * | 2/2015 | Nikou ................ | A61B 17/1633 606/130 |
| 2005/0216032 A1 * | 9/2005 | Hayden ............. | A61B 17/1725 606/86 R |
| 2006/0142657 A1 * | 6/2006 | Quaid ................... | A61B 90/37 600/424 |
| 2008/0033442 A1 | 2/2008 | Amiot et al. | |
| 2011/0208093 A1 * | 8/2011 | Gross .................... | A61B 90/10 600/587 |
| 2012/0010710 A1 | 1/2012 | Frigg | |
| 2013/0060278 A1 * | 3/2013 | Bozung ............. | A61B 17/1675 606/205 |
| 2016/0125603 A1 | 5/2016 | Tanji | |

* cited by examiner

SYSTEM AND METHOD FOR INSTALLING BONE HARDWARE OUTSIDE AN END-EFFECTORS TOOL PATH

TECHNICAL FIELD

The present invention generally relates to the field of computer-assisted orthopedic surgery, and in particular to installing hardware on a bone at locations that will avoid colliding with an end-effector tool of a computer-assisted orthopedic device as the end-effector tool prepares the bone to receive an implant.

BACKGROUND

Throughout a lifetime, bones and joints become damaged and worn through normal use, disease, traumatic events, or a combination thereof. Arthritis is a leading cause of joint damage that leads to cartilage degradation, pain, swelling, stiffness, and bone loss overtime. Arthritis can also cause the muscles articulating the joints to lose strength.

If the pain associated with the dysfunctional joint is not alleviated by less-invasive therapies, a joint arthroplasty procedure is considered as a treatment. Joint arthroplasty is an orthopedic procedure in which an arthritic or dysfunctional joint surface is replaced with an orthopedic prosthesis.

The accurate placement and alignment of an implant is a large factor in determining the success of joint arthroplasty. Even a slight misalignment of the implant may result in poor wear characteristics, reduced functionality, decreased prosthetic longevity, or a combination thereof.

In order to achieve accurate implant placement and alignment, a cutting tool (e.g., a saw, drill, end-mill, reamer) is accurately positioned relative to the bone prior to making any bone cuts and/or modifications. In some methods, a cutting jig or alignment guide may be used to accurately position and orient a cutting tool. In still other conventional methods, the cuts may be made using a computer-assist device (e.g., a surgical robot) that controls a cutting tool. When a computer-assist device is used to make the cuts, the bone's position and orientation (POSE) must be known precisely in three-dimensional space relative to the computer-assist device to ensure that the cuts and/or modifications are made in the correct location. Several methods to determine the POSE of a bone relative to a computer-assist device are known in the art such as the registration methods described in U.S. Pat. Nos. 6,033,415 and 5,951,475.

However, bone motions during the process of cutting may generate cutting inaccuracies during the procedure if the bone is assumed to be fixed with respect to the computer-assist device. Should a sufficient amount of bone motion occur, it is then necessary to immediately stop the cutting operation and restart the cutting procedure after re-locating the position of the bone with respect to the computer-assist device.

In order to facilitate the process of restoration of the registration after bone motion occurs, a system and method using recovery markers placed on the bone may be employed as described in U.S. Pat. No. 6,430,434. These recovery markers can be used to re-register the bone and track bone motion over time by simply re-digitizing the location of the recovery markers. In this conventional method however, a user installs the recovery markers at any desired location and depth on the exposed bone. Therefore, the recovery markers may be unknowingly installed at a position on the bone that may collide with autonomous or semi-autonomous movements of an end-effector tool controlled by a robotic arm. The placement of a portion of the recovery marker so as to be unintentionally positioned in the tool path of the end-effector can prove problematic. If the end-effector collides with the recovery marker while preparing the bone to receive the prosthesis, several problems can arise, illustratively including: the procedure being interrupted; the end-effector may be damaged in the collision; and the recovery marker now needs to be removed from the bone, re-installed at a new location, and the bone fully re-registered before the procedure can continue. In the event that any of these problems occurs, the procedure is delayed and the patient subjected to additional time under anesthesia.

It will be appreciated that many other orthopedic procedures require the use of hardware to be installed on the bone. For example, a computer-assisted surgical system may require the use of tracking array to be installed on the bone to track the bone with an optical tracking system. It is just as likely for the tracking array to be installed in an end-effectors toolpath.

Thus, there is a need in the art for a system and method to aid a surgical team in installing hardware on a bone outside an end-effectors tool path prior to modifying the bone.

SUMMARY OF THE INVENTION

A method for installing hardware in a bone at locations outside and tool path of an end-effector prior to modifying the bone are described herein. The method includes the installation of a piece of hardware in the bone. The position of the bone and a cut volume is register to a computer-assist device. A first position of the first piece of hardware is digitized with a digitizer probe having a probe tip. A processor calculates a first position of the first piece of hardware relative to the cut volume. A user is notified if the first piece of hardware is at or inside the cut volume based on the calculation. If the first piece of hardware is at or inside the cut volume, a second piece of hardware is installed in the bone. The second piece of hardware is digitized. The processor calculated a second position of the second piece of hardware relative to the cut volume. If the second piece of hardware is outside the cut volume, then the second piece of hardware is used for a computer-assisted surgical procedure.

The first piece of hardware may be a first set of recovery markers and the second piece of hardware may be a second set of recovery markers. The method may then include the installation of the first set of recovery markers in the bone. A position of the bone and a cut volume are register to a computer-assist device. A first position of the first recovery markers are digitized with digitizer probe having a probe tip. A processor calculates a first position of one or more recovery markers in the first set of recovery markers relative to the cut volume. A user is notified if the first set of recovery is at or inside the cut volume of the bone based on the calculations. A second set of recovery markers are installed in the bone if one or more markers in the first set of recovery markers are inside the cut volume. The first set of recovery markers remain in the bone for re-registration if the bone moves while installing the second set of recovery markers. The second set of recovery markers are digitized. The processor calculates if one or more markers in the second set of recovery markers is at or inside the cut volume. If the second set of markers are outside the cut volume, the first set of marker are removed and the second set of markers are used for re-registration during the surgical procedure.

A system for implementing the above method is also described herein. The system includes the following. One or more pieces of hardware are provided to be installed in the bone. A computer-assisted surgical system having a processor and memory for executing a surgical procedure. The memory has a surgical plan stored therein having a cut volume defined relative to a bone model. A digitizer is in communication with the surgical system for collecting point in physical space. The memory further includes one or more software modules to be executed by the processor. The one or more software modules when executed by the processor cause the processor to perform the following actions. Register the cut volume relative to the bone based on a plurality of points collected on the bone by the digitizer. Calculate a first position of a first piece of hardware installed in the bone relative to the cut volume based on one or more points digitized on the first piece of hardware. Notify a user if the first piece of hardware is at or inside the cut volume of the bone based on the calculations. Instruct the user to install a second piece of hardware in the bone if the first piece of hardware is at or inside the cut volume. Calculate if the second piece of hardware installed in the bone is at or inside the cut volume. Execute a surgical task if the second piece of hardware is outside the cut volume as determined by the calculation.

BRIEF DESCRIPTION OF THE DRAWINGS

Examples illustrative of embodiments of the present invention are described below with reference to figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures are listed below.

FIGS. 4A-4B, visually depicts an algorithm to determine if a recovery marker is located inside a volume of bone to be removed (i.e., a cut volume) in accordance with embodiments of the invention, where

FIGS. 5A-5C depict several feedback mechanisms to notify a user when a set of recovery markers are located on or inside a cut volume, where

DETAILED DESCRIPTION OF THE INVENTION

The present invention has utility as a system and method for aiding a surgical team in installing a set of recovery markers on a bone at locations outside an end-effector's tool path prior to modifying the bone. The present invention has further utility in providing the surgical team with the ability to re-register the bone in the event bone motion occurs while installing a second set of recovery markers on the bone, if needed. It should be appreciated, that although the installation of recovery markers is described herein, the method is equally useful and advantageous for installing other hardware (e.g., optical tracking arrays) on the bone at locations that ensure the hardware is installed outside of an end effector's tool path.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

Definitions

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

As used herein, the term "recovery marker" refers to a physical reference marker designed to permit a measurement system, such as a mechanical tracking system, optical tracking system, electro-magnetic tracking system, ultrasound tracking system, and/or an imaging system (e.g., computed tomography (CT), X-ray, fluoroscopy, ultrasound, magnetic resonance imaging (MRI)), to determine at least one of a position or orientation of at least a portion of the reference marker.

As used herein, the term "registration" refers to the determination of the spatial relationship between two or more objects or coordinate systems such as a computer-assist device and at least one of a bone, or an image data set of a bone. "Re-registration" refers to any subsequent registration procedure that occurs after an initial registration and is executed with the use of the recovery markers.

As used herein, the term "cut volume" refers to a volume of a bone to be removed by a computer-assist device.

As used herein, the term "digitizer" refers to a measuring device capable of measuring physical coordinates in three-dimensional space. Examples of a "digitizer" include a high-resolution electro-mechanical sensor arm as described in U.S. Pat. No. 6,033,415, an optically tracked probe as described in U.S. Pat. No. 7,043,961, an end-effector of a robotic system, and similar measuring devices that may be tracked by other tracking systems known in the art.

As used herein, the term "digitizing" refers to the collection, recordation, or measurement of one or more physical coordinates in three-dimensional space.

As used herein, the term "real-time" refers to processor in which input data is processed within milliseconds such that calculated values are available within 10 seconds of computational initiation.

Also, referenced herein are computer-assist devices, which may also be referred to as computer-assisted devices, computer-assisted surgical systems, and robotic surgical systems. Examples of computer-assist devices illustratively include a 1-N degree of freedom hand-held surgical system, an optical tracking system tracking one or more tools (e.g., tracked instruments, manipulator arms) in space, a navigated surgical system, a serial-chain manipulator system, a parallel robotic system, or a master-slave robotic system, as described in U.S. Pat. Nos. 5,086,401, 6,033,415, 7,206,626, 8,876,830 and 8,961,536, U.S. Pat. App. No. 2013/0060278, 2005/0216032 and U.S. Prov. App. No. 62/054,009 all of which are incorporated by reference herein in their entirety. The computer-assisted surgical system may provide autonomous, semi-autonomous, haptic, or no (passive) control, or any combination thereof.

While the present invention is illustrated visually hereafter with respect to a femur as the bone for which the recovery markers are installed and to which the present invention is applied, it is appreciated that the present invention is equally applicable to other bones of a human, non-human primate, or other mammals.

Figure 1:
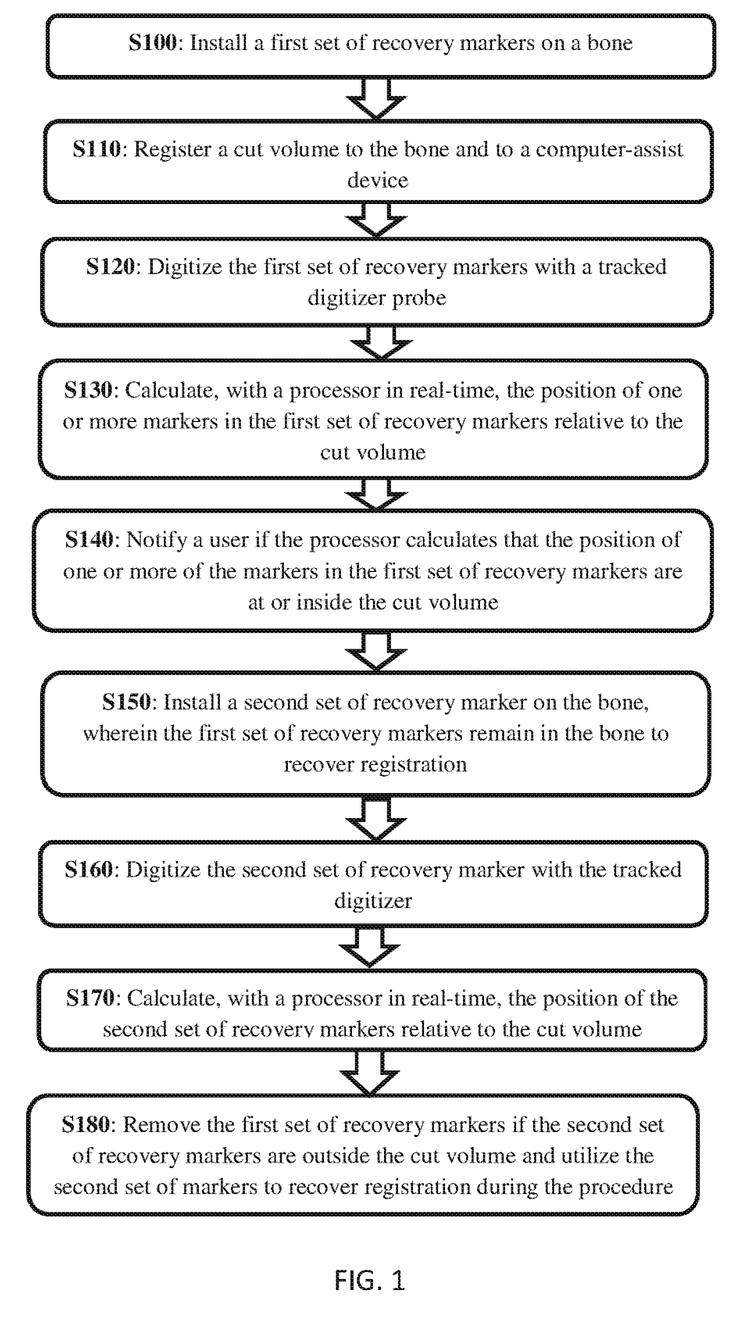
FIG. 1 depicts a flowchart of a method to aid a surgical team in installing a set of recovery markers at one or more locations on a bone that ensures the markers avoid colliding with an end-effector tool of a computer-assisted device.

With reference to the figures, FIG. 1 depicts a method for installing one or more recovery markers on a bone to avoid a potential collision with an end-effector tool of a computer assist device. The method generally includes: installing a first set of recovery markers on a bone (S100); registering a bone and a cut volume to a computer assist device (S110); digitizing the first set of recovery markers with a tracked digitizer probe (S120); calculating, with a processor in real-time, the position of one or more recovery markers in the first set of recovery markers relative to a cut volume (S130); notifying a user whether the first set of recovery markers are at or inside the cut volume of the bone based on the calculations (S140); installing a second set of recovery marker on the bone, wherein the first set of recovery markers remain in the bone to re-register the bone if there is bone motion while installing the second set of recovery markers on the bone; (S150); digitizing the second set of recovery marker with the tracked digitizer probe (S160); calculating, with a processor in real-time, the position of one or more recovery markers in the second set of recovery markers relative to the cut volume (S170); removing the first set of recovery markers if the second set of recovery markers are outside the cut volume and utilizing the second set of recovery markers during the procedure to recover the registration (S180). Specific embodiments of the method and components are further described in detail below.

Figure 2A:
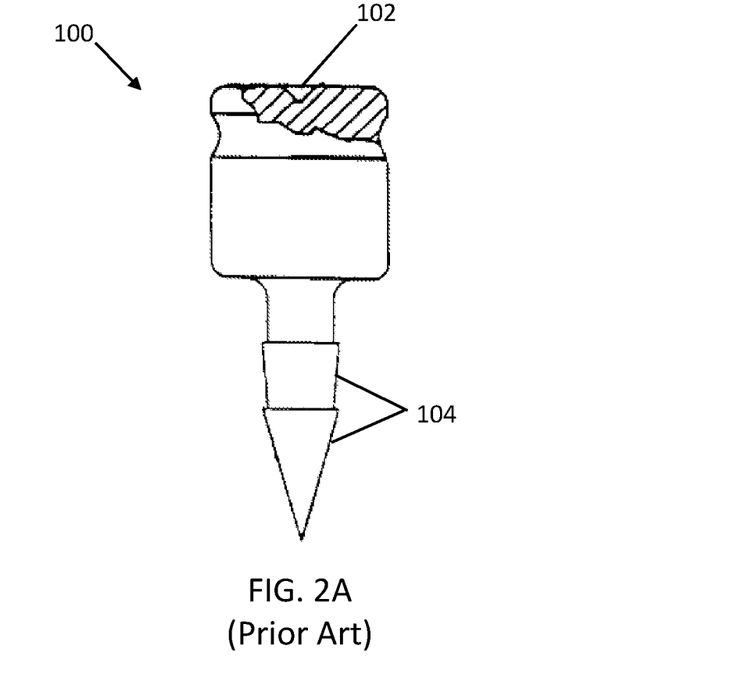
FIG. 2A depicts a prior art point recovery marker.
Figure 2B:
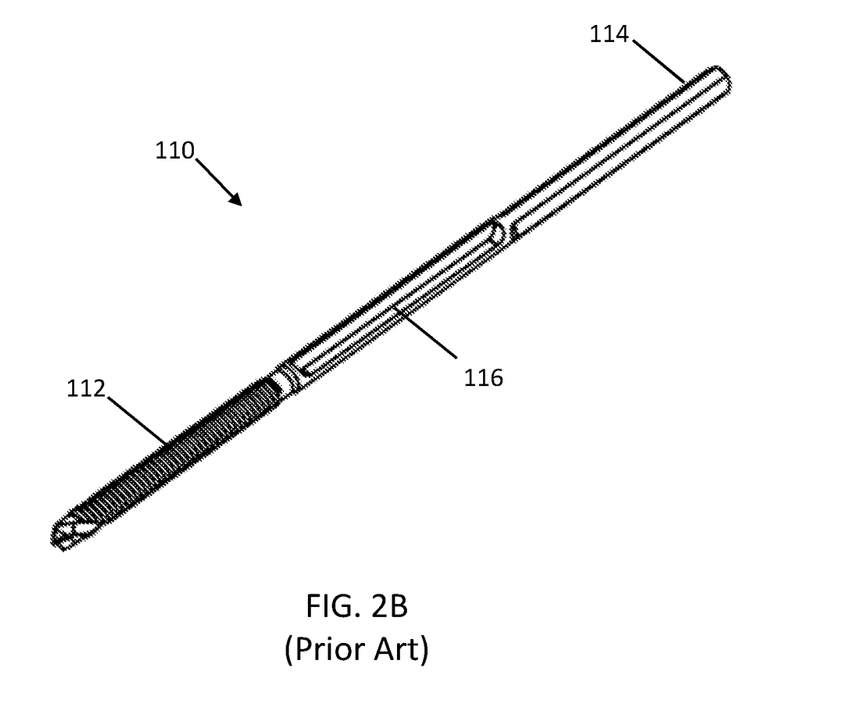
FIG. 2B depicts a prior art groove recovery marker.

With reference to FIGS. 2A and 2B, a prior art example of a set of recovery markers is shown including a point recovery marker 100 shown in FIG. 2A and a groove recovery marker 110 shown in FIG. 2B. The point recovery marker 100 is described in U.S. Pat. No. 6,430,434. The point recovery marker 100 generally includes a divot 102 for facilitating the collection of a fixed point, and a bone-engaging portion 104 for engaging a bone. The groove recovery marker 110 includes a bone-engaging portion 112, a proximal portion 114, and a groove 116 between the bone-engaging portion 112 and the proximal portion 114. The bone-engaging portion 112 of the groove recovery marker 110 may include threads or flutes to grasp the bone. A driver tool, such as a screwdriver or drill, may receive the proximal portion 114 to aid in driving the groove recovery marker 110 into the bone. The groove 116 facilitates the collection of a series of points along the length of the groove 116. A method for re-registering a bone using the point recovery marker 100 and groove recovery marker 110 is described in U.S. Prov. Pat. App. 62/302,733 filed Mar. 2, 2016 assigned to the assignee of the present application and incorporated by reference herein in its entirety.

Figure 3:
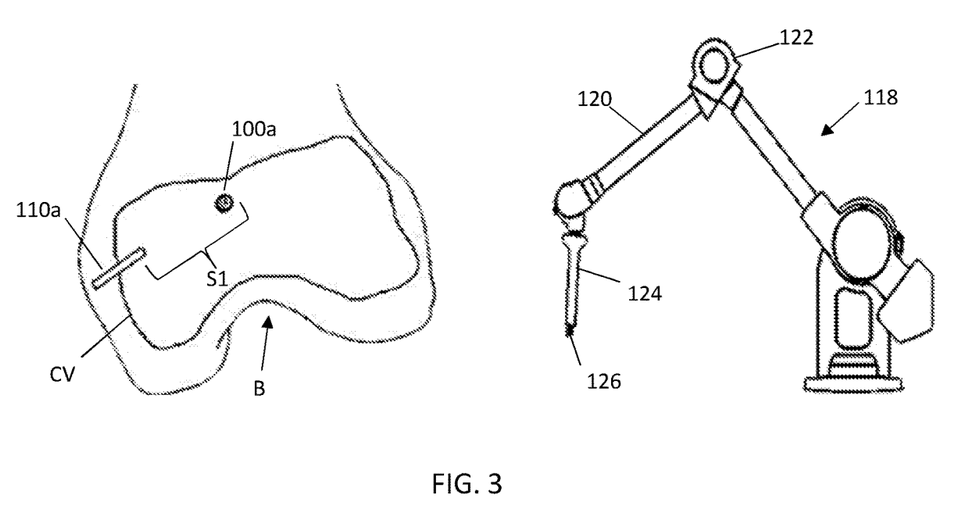
FIG. 3 depicts a first set of recovery markers installed on a bone at a location inside a volume of bone to be removed in accordance with embodiments of the invention.

In a particular inventive embodiment, with respect to FIG. 3, a bone B is shown having a point recovery marker 100a and a groove recovery marker 110a installed therein at two locations, respectively, corresponding to step S100 of FIG. 1. The point recovery marker 100a and groove recovery marker 110a make-up a first set of recovery markers (S1). A set of recovery markers is needed to establish a coordinate system on the bone to re-register the bone if bone motion occurs. Here, the point recovery marker 100a and the groove recovery marker 110a act as the first set of recovery marker installed on the bone B, however it should be appreciated that any combination and number of recovery markers (e.g., three point recovery markers) may be installed on the bone B and act as a set of recovery markers without deviating from the scope of the invention.

A cut volume CV of the bone to be removed is then registered to the bone B and the computer-assist device using techniques known in the art corresponding to step S110. In a particular embodiment, the POSE of the cut volume CV relative to the bone B is defined in a pre-operative planning workstation, where a user plans the position and orientation (POSE) of a virtual implant model relative to virtual bone model. The location of the cut volume CV is then defined as the intersection of the virtual implant model with the virtual bone model. The cut volume CV itself, may have a volume corresponding to the volume of the virtual implant model intersecting with virtual bone model; however, it should be appreciated a user or technician may adjust the size or geometry of the cut volume CV to accomplish one or more specific goals (e.g., reduce the cut volume relative to the volume of the implant model to create a press-fit between the actual implant installed in a prepared bone). After the user plans the POSE of the virtual implant model/cut volume relative to the virtual bone model, the plan is transferred to the computer-assisted device and registered to the bone B such that the computer-assist device knows where to remove the bone B according to the cut volume CV.

As shown in FIG. 3, the user has unknowingly installed the point recovery marker 100a and groove recovery marker 110a at locations where at least a portion of the point recovery marker 100a and groove recovery marker 110a intersect inside the cut volume CV. The cut volume CV is shown as a bounding line on the bone B representing where a computer-assist device will remove bone. Note, that the user has no knowledge of where the cut volume CV is located, and only the computer-assist device knows where to remove bone according to the cut volume CV after registration.

Also shown in FIG. 3 is a detailed view of a mechanical digitizer 118 for digitizing the bone and the recovery markers. The mechanical digitizer 118 includes articulating links 120 joined by joints 122, and a probe 124 having a probe tip 126 attached to a distal link of the digitizer 118. Each joint has encoders to determine at least one of a position and orientation of the probe tip 126 in three-dimensional space. In a specific embodiment, the mechanical digitizer 118 is integrated to the base of a robotic arm and registered to a robotic arm as described in U.S. Pat. No. 6,033,415. Although a mechanical digitizer 118 is shown and described in detail in FIG. 3, it should be appreciated that the other aforementioned digitizers (e.g., optically tracked digitizer probe) may measure, collect, and record points in physical space.

In a particular inventive embodiment, corresponding with step S120 of FIG. 1, a digitizer is used to digitize the point recovery marker 100a and the groove recovery marker 110a of the first set of recovery markers S1 to: i.) establish a bone coordinate system to recover the registration; and ii.) aid in the determination of the entire POSE of the point recovery marker 100a and the groove recovery marker 110a in physical space, where the POSEs are used by the processor to calculate if one or more of the recovery markers (100a, 110a) are at least partially installed inside the cut volume CV. In a specific embodiment, the bone coordinate system is determined as described in PCT/US2017/020175 and/or U.S. Pat. No. 6,430,434 both assigned to the assignee of the present application and incorporated by reference herein in their entirety. To aid in the determination of the POSE of the point recovery marker 100a and the groove recovery marker 110a in physical space, the user digitizes the top of the point recovery marker 100a (e.g., the divot 102) and the top of the groove recovery marker 110a (e.g., the most proximal point, or end, of the proximal portion 114). The user then aligns a longitudinal axis of the digitizer probe 124 with a longitudinal axis of the point recovery marker 100a and a longitudinal axis of the groove recovery marker 110a to collect the orientation of the point recovery marker 100a and the groove recovery marker 110a, respectively, in physical space. By knowing: a. where the top of each recovery marker (100a and 110a) is located; b. the orientation of each recovery marker (100a and 110a); and c. the length of each recovery marker (100a and 110a), then the POSE of each recovery marker (100a and 110a) is precisely known in physical space. The length of each recovery marker (100a and 110a) is known based on manufacturing specifications and stored in the computer-assist device memory. The diameter of the recovery markers (100a and 110a) may further be stored in memory, to further define the volume that the recovery markers (100a and 110a) occupy in physical space, which may be accomplished by modeling the recovery markers (100a and 110a) as cylinders. By knowing the POSE of each recovery marker (100a and 110a) in physical space, and optionally the volume, the processor can calculate if a portion of either recovery marker (100a and/or 110a) is at or inside the cut volume CV as further described below.

Figure 4A:
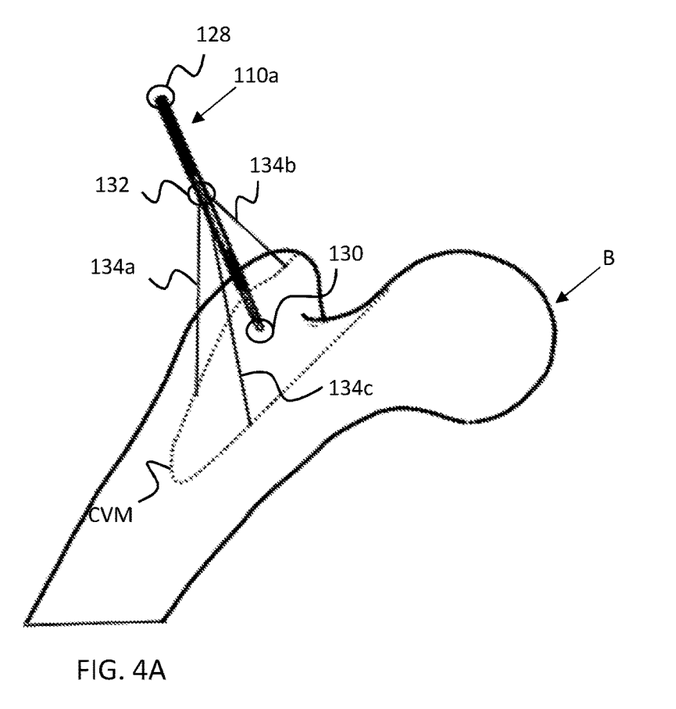
FIG. 4A depicts the relative distance of a first point on the recovery marker relative to the cut volume.
Figure 4B:
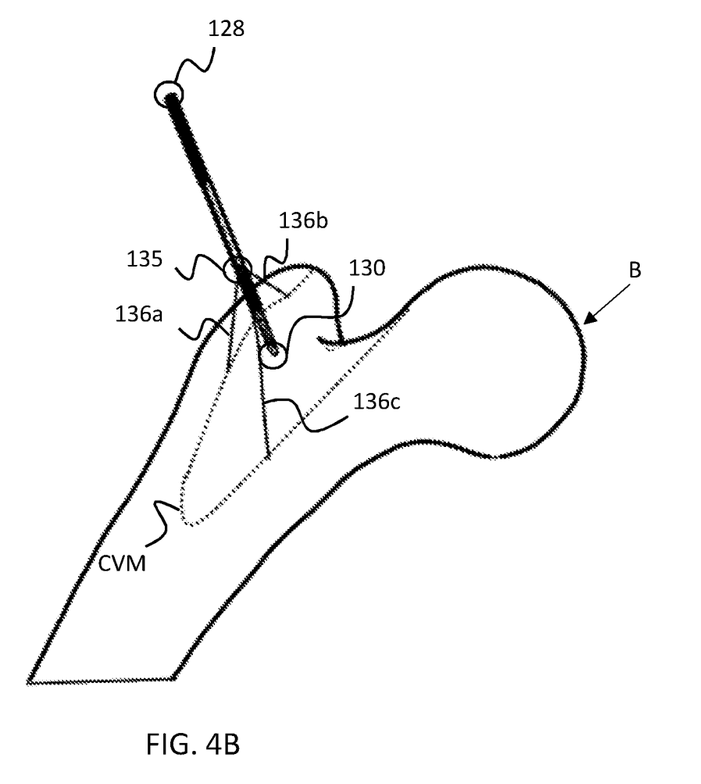
FIG. 4B depicts the relative distance of a second point on the recovery marker relative to the cut volume.

Corresponding with step S130 of FIG. 1, a processor associated with at least one of a digitizer or a computer-assisted surgical device, calculates the position and orientation (POSE) of: a.) the point recovery marker 100a relative to the cut volume CV; and b.) the groove recovery marker 110a relative to the cut volume (CV). With reference to FIGS. 4A and 4B, a particular embodiment of a method to determine the POSE of the recovery markers (100a, 110a) relative to the cut volume CV is illustrated with a groove recovery marker 110a installed in the proximal femur. As only a groove recovery marker 110a is shown in this example, the same procedure may be used for the point recovery marker 100a and other installed hardware. To begin, the POSE of the groove recovery marker is determined in physical space with the aforementioned techniques (e.g., a proximal end 128 of the groove recovery marker 110a is digitized, an orientation of the groove recovery marker 110a is determined, and a distal end 130 of the groove recovery marker 110a is determined by knowing the location of the proximal end 128, the orientation of the marker 110a, and the length of the marker 110a). Therefore, the entire body of the marker 110a is known in physical space. Next, in one embodiment, the entire body of the marker 110a in physical space is transformed to the coordinate system of the cut volume CV stored in the computer-assist device to compare the POSE of the marker 110a relative to the cut volume CV in the same coordinate system. In another embodiment, the calculations are performed in the physical space coordinate system with the cut volume CV registered to the physical location of the bone B. A cut volume virtual model may also be generated representing the outer boundaries of the cut volume CV to aid in the calculations. In any case, the POSE of the recovery marker 110a is then examined relative to the cut volume CV or cut volume virtual model using an algorithm. In a specific inventive embodiment, the algorithm is a point-distance algorithm that measures the distance of all the points on the recovery marker 110a from the cut volume CV or cut volume model CVM. For example, as shown in FIG. 4A, a first point 132 on the recovery marker 110a is examined to determine the distance between the first point 132 and any point on a cut volume model CVM. The lines 134a, 134b, and 134c illustrate the distance of the first point 132 relative to three points on the cut volume model CVM. With reference to FIG. 4B, a second point 135 on the recovery marker 110a is subsequently examined to determine the distance between the second point 135 and any point on the cut volume model CVM. The lines 136a, 136b, and 136c, likewise illustrate distances between the second point 135 relative to three points on the cut volume model CVM. The point-distance algorithm performs the distance calculations for points along the entire length of the marker 110a relative to the entire volume of the cut volume CV or coverage area of the cut volume model CVM. If a calculated distance between a point on the marker 110a and the cut volume model CVM is below a threshold distance, then the computer-assist device warns or alerts the user that the recovery marker 110a is inside the cut volume CV. In some embodiments, the threshold distance is less than 1 mm.

Figure 5A:
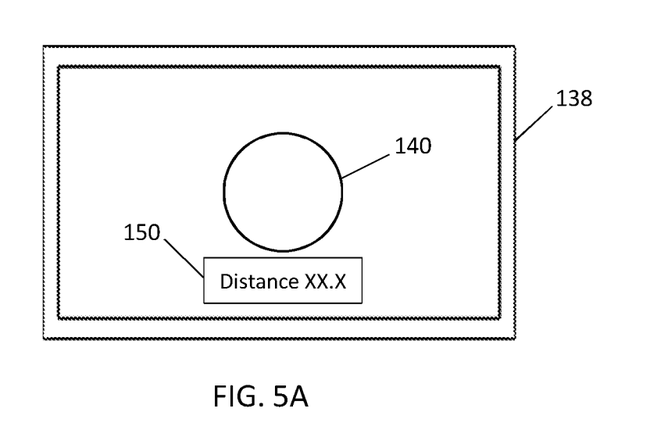
FIG. 5A depicts a visual signal.
Figure 5B:
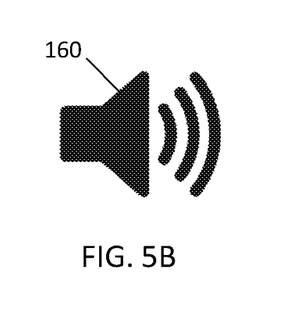
FIG. 5B depicts an audible signal.
Figure 5C:
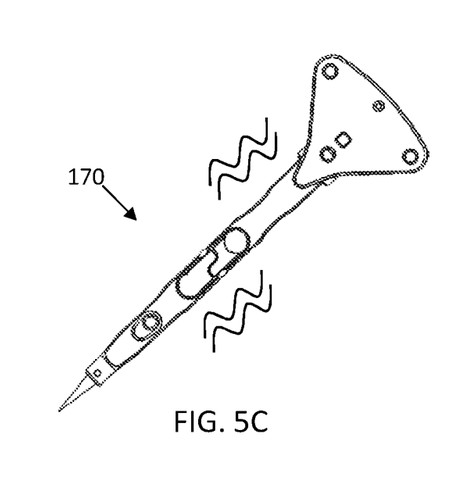
FIG. 5C depicts a haptic signal in accordance with embodiments of the invention.

Corresponding with step S140 in FIG. 1 and with reference to FIGS. 5A-5C, a feedback mechanism notifies a user if the first set of recovery markers S1 is located at, inside, or outside the cut volume. In more detail as shown in FIG. 5A, the feedback may be provided in the form of a visual signal 140 displayed on a monitor 138. The visual signal 140 may include a variety of lights, a written notification, a symbol notification, or any indicia equivalent thereof. In a specific embodiment, the monitor 138 may also include a distance calculator visual display 150. The distance calculator visual display 150 may calculate and visually notify the user of the calculated distance between one or more points on a recovery marker (100, 110) relative to the cut volume CV. With reference to FIG. 5B, the feedback may be provided in the form of an acoustic signal 160. The acoustic signal 160 may further include a variety of audible notification sounds illustrative including a beeping sound, a vocal sound, or a combination thereof. With reference to FIG. 5C, the feedback may be provided in the form of a haptic signal 170. The haptic signal 170 may be in any form of a vibration or other imposed force on the user. Here, it should be appreciated that the feedback system may be in the form of any of acoustic, motion, visual signals, or a combination thereof.

Figure 6:
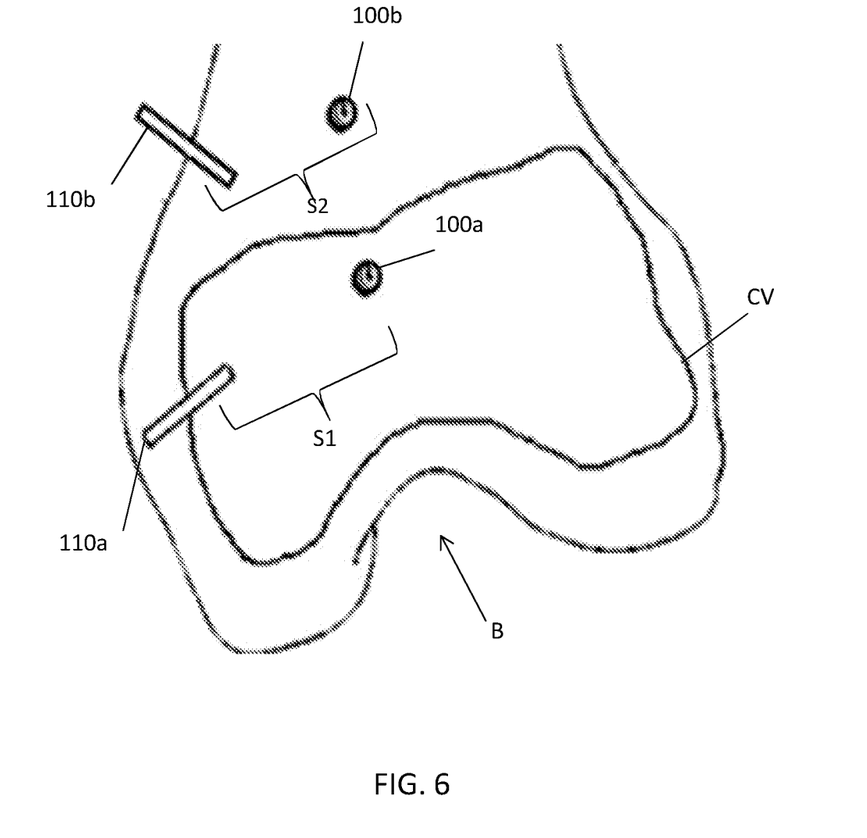
FIG. 6 depicts a first set of recovery markers installed on a volume of bone to be removed and a second set of recovery markers installed outside of a volume of bone to be removed in accordance with embodiments of the invention.

Corresponding with step S150 of FIG. 1 and as shown in FIG. 6, if a portion of one or more recovery markers (100a, 110a) in the first set of recovery markers S1 is determined to exist at or inside the cut volume CV, a user is prompted to install a second set of recovery markers S2 on the bone B, while leaving the first set of recovery markers S1 in the CV of the bone. A bone coordinate system was established with the first set of recovery markers S1 such that the user can re-register the bone B if bone motion occurs while the second set of recovery markers S2 are being installed and/or digitized. The user attempts to install the second set of recovery markers S2 outside the cut volume CV. Corresponding to step S160 in FIG. 1 a user then digitizes the second set of recovery markers S2 to: i.) establish a bone coordinate system to recover the registration with the second set of recovery markers S2; and ii.) aid in the determination of the entire POSE of the point recovery marker 100a and the groove recovery marker 110a in physical space, where the POSEs are used by the processor to calculate if one or more of the second set of recovery markers (100a, 110a) is at least partially installed inside the cut volume CV. Corresponding to step S170 in FIG. 1, a processor then calculates, in real-time, the position of the second set of recovery markers S2 relative to the cut volume. It should be appreciated that the method of digitizing the second set of recovery markers S2 and calculating the position of the second set of recovery markers S2 relative to the cut volume CV is the same method as described above in steps S120-S130 for the first set of recovery markers S1.

In a particular inventive embodiment, the method described herein further includes the assembly of a bone motion monitor to the bone B prior to bone registration. The bone motion monitor may be a probe disposed on the bone and in communication with a 3 to 6 degree-of-freedom strain gauge, or other force sensor, to detect if motion occurs beyond a specific threshold. If bone motion is detected while installing the second set of recovery markers S2, then the user is notified to re-register the bone with the first set of recovery markers S1 using the methods described in PCT/US2017/020175 and/or U.S. Pat. No. 6,430,434. After re-registration, the user is prompted to continue installing the second set of recovery markers S2.

In a particular inventive embodiment, the computer-assist device may assist the user in locating one more locations to install one or more secondary recovery markers (100b, 110b) such that the markers (100b, 110b) are outside of the cut volume CV. In one embodiment, the user may use a digitizer, such as the mechanical digitizer 118, to probe around the bone B to search for a suitable location. For example, if the processor calculated that a portion of a first groove recovery marker 110a was installed having 3 mm of the marker 110a inside the cut volume CV, then a suitable location may be 4 mm in a particular direction. Then, when the digitizer is probed 4 mm in the appropriate direction and outside the cut volume CV, then the computer-assist device provides a signal indicating so. The user may then install a second recovery marker (100b, 110b) in that location. A more detailed description of probing the bone B with a digitizer to find a location to install hardware is described in U.S. Provisional Pat. App. 62/446,719 assigned to the assignee of the present application. In another inventive embodiment, the monitor 138 may provide visual instructions to the user. The monitor 138 may display a representation of the POSE of the first set of recovery markers S1 relative to the cut volume CV and highlight where or how the first point recovery marker 100a and/or first groove recovery marker 110b is positioned relative to the cut volume CV. The user then has a reference (i.e., the POSE of the first set of recovery markers S1 installed in the bone relative to the cut volume CV) to install the second set of recovery markers S2 outside of the cut volume CV.

Corresponding to step S180 in FIG. 1, if the calculated position of the second set of recovery markers S2 is outside the cut volume CV, then the user may remove the first set of recovery markers S1 and proceed with the surgical procedure (i.e., modifying the bone B) without worry that the set of recovery markers S2 will collide with the modifying tool (e.g., an end-effector tool of a surgical robot). The user may then use the second set of recovery markers S2 to recover the registration, if needed. However, if the processor calculates that a portion of one or more of the second recovery markers (100b, 110b) in the second set of recovery markers S2 is inside the cut volume CV, then the same process is repeated with a third set of recovery markers S3 and so on, until a set of recovery markers SN is located outside the cut volume CV.

Tracking Arrays and Other Hardware

Figure 7:
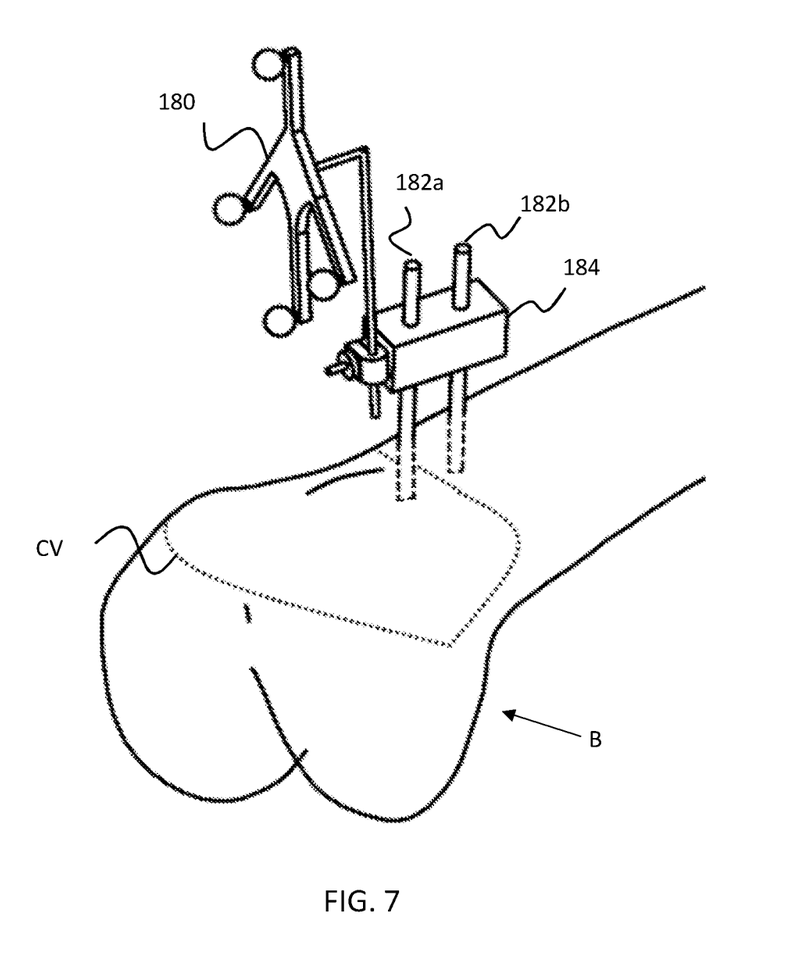
FIG. 7 depicts a tracking array installed inside a volume of bone to be removed in accordance with embodiments of the invention.

The method described herein may be adapted to aid a user in installing other hardware on a bone B to ensure the hardware is installed outside a cut volume prior to modifying the bone B. In a particular inventive embodiment, with reference to FIG. 7, a tracking array 180 is shown installed on a bone B via pins (182a, 182b). One or more pins (182a, 182b) are inserted into the bone B and an assembly block 184 assembles or attaches the pins (182a, 182b) to the tracking array 180. The tracking array 180 permits the bone B to be tracked by an optical tracking system in real-time. However, the one or more of the pins (182a, 182b) may be installed inside a cut volume CV. Therefore, the method described above may be used to ensure that one or more pins (182a, 182b) are not installed at or inside the cut volume CV prior to modifying the bone. The pins (182a, 182b) in conjunction with a checkpoint (not shown) may also be used to re-register the bone if the tracking array 180 moves relative to the bone B during the procedure using the tracking array registration recovery method as described in PCT/US2017/020175.

Computer-Assist Device

Figure 8:
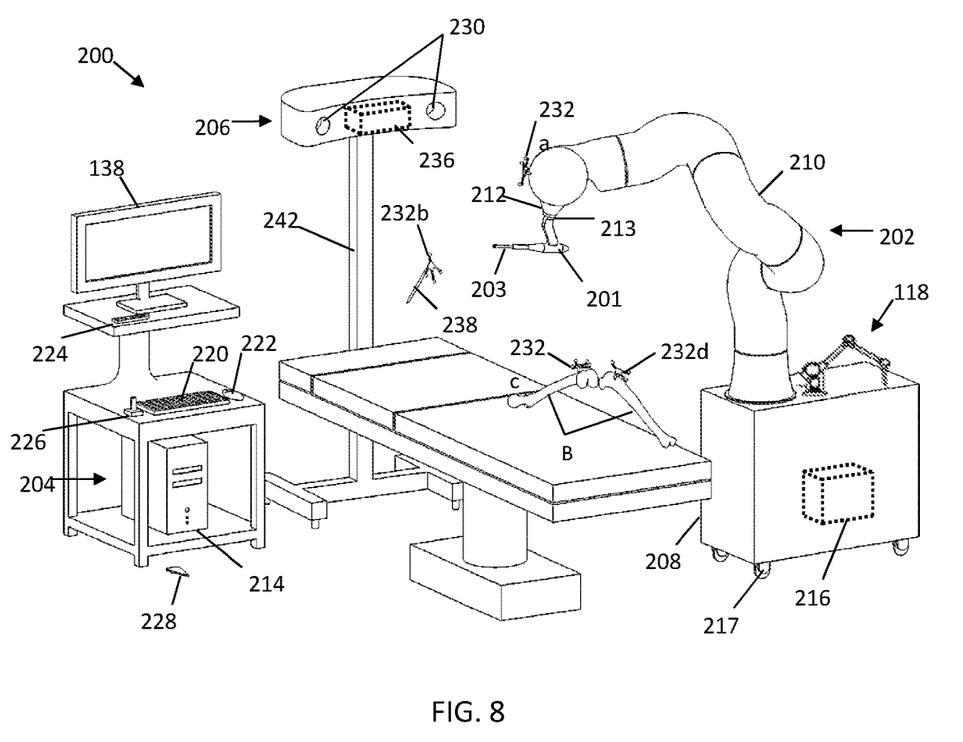
FIG. 8 illustrates a surgical system in the context of an operating room (OR) in accordance with embodiments of the invention.

With reference to FIG. 8, an embodiment of a computer-assist device, and more specifically a robotic surgical system is shown generally at 200 capable of implementing embodiments of the inventive method described herein is shown in the context of an operating room (OR). The surgical system 200 generally includes a surgical robot 202, a computing system 204, and includes at least one of a mechanical digitizer 118 or a non-mechanical tracking system 206 (e.g., optical tracking system). The end-effector of the surgical robot 202 may also have the capabilities of the mechanical digitizer 118 directly, where the mechanical digitizer 118 is no longer needed.

The surgical robot 202 may include a movable base 208, a manipulator arm 210 connected to the movable base 208, an end-effector flange 212 located at a distal end of the manipulator arm 210, and an end-effector assembly 201 for holding and/or operating an end-effector tool 203 removably attached to the flange 212 by way of an end-effector mount 213. The movable base 208 in some inventive embodiments includes a set of wheels 217 to maneuver the movable base 208, which may be fixed into position using a braking mechanism such as a hydraulic brake. The manipulator arm 210 includes various joints and links to manipulate the tool 203 in various degrees of freedom. If the mechanical digitizer 118 is not present, the end effector assembly 201 may be fitted with a probe to act as a digitizer directly. The joints are illustratively prismatic, revolute, spherical, or a combination thereof.

The computing system 204 generally includes a planning computer 214; a device computer 216; an optional tracking computer 236 if a tracking system 206 is present; and peripheral devices. The planning computer 214, device computer 216, and tracking computer 236, may be separate entities, single units, or combinations thereof depending on the surgical system. The peripheral devices allow a user to interface with the surgical system components and may include: one or more user-interfaces, such as a display or monitor 138; and user-input mechanisms, such as a keyboard 220, mouse 222, pendent 224, joystick 226, foot pedal 228, or the monitor 138 where in some inventive embodiments the monitor 138 has touchscreen capabilities.

The planning computer 214 contains hardware (e.g., processors, controllers, and memory), software, data and utilities that are in some inventive embodiments dedicated to the planning of a surgical procedure, either pre-operatively or intra-operatively. This may include reading medical imaging data, segmenting imaging data, constructing three-dimensional (3D) virtual models, storing computer-aided design (CAD) files, providing various functions or widgets to aid a user in planning the surgical procedure, and generating surgical plan data. The final surgical plan includes operational data for modifying a volume of tissue that is defined relative to the anatomy, such as a set of points in a cut-file to autonomously modify the volume of bone to be removed (i.e., cut volume), a set of virtual boundaries defined to haptically constrain a tool within the defined boundaries (i.e., cut volume) to modify the bone, a set of planes or drill holes to drill pins in the bone, or a graphically navigated set of instructions for modifying the tissue. The surgical plan data in some inventive embodiments also includes instructions for the end-effector assembly 201 to control the tool 203. The data generated from the planning computer 214 may be transferred to the device computer 216 and/or tracking computer 236 through a wired or wireless connection in the operating room (OR); or transferred via a non-transient data storage medium (e.g., a compact disc (CD), a portable universal serial bus (USB) drive) if the planning computer 214 is located outside the OR.

The device computer 216 in some inventive embodiments may be housed in the moveable base 208 and contain hardware, software, data and utilities that are preferably dedicated to the operation of the surgical device 202 to execute a surgical task. This may include surgical device control, robotic manipulator control, the processing of kinematic and inverse kinematic data, the execution of registration algorithms, the execution of calibration routines, the execution of surgical plan data, coordinate transformation processing, providing workflow instructions to a user, utilizing position and orientation (POSE) data from the tracking system 206, and executing algorithms to determine if one or more recovery markers (100, 110) or other hardware is installed inside a cut volume.

The optional tracking system 206 of the surgical system 200 includes two or more optical receivers 230 to detect the position of fiducial markers (e.g., retroreflective spheres, active light emitting diodes (LEDs)) uniquely arranged on rigid bodies. The fiducial markers arranged on a rigid body are collectively referred to as a tracking array 232, where each tracking array 232 has a unique arrangement of fiducial markers, or a unique transmitting wavelength/frequency if the markers are active LEDs. An example of an optical tracking system is described in U.S. Pat. No. 6,061,644. The tracking system 206 may be built into a surgical light, located on a boom, a stand 242, or built into the walls or ceilings of the OR. The tracking system computer 236 may include tracking hardware, software, data and utilities to determine the POSE of objects (e.g., bones B, surgical device 204) in a local or global coordinate frame. The POSE of the objects is collectively referred to herein as POSE data, where this POSE data may be communicated to the device computer 216 through a wired or wireless connection. Alternatively, the device computer 216 may determine the POSE data using the position of the fiducial markers detected from the optical receivers 230 directly.

The POSE data is determined using the position data detected from the optical receivers 230 and operations/processes such as image processing, image filtering, triangulation algorithms, geometric relationship processing, registration algorithms, calibration algorithms, and coordinate transformation processing. For example, the POSE of a digitizer probe 238 with an attached probe tracking array 232b may be calibrated such that the probe tip is continuously known as described in U.S. Pat. No. 7,043,961. The POSE of the tool tip or tool axis of the tool 203 may be known with respect to a device tracking array 232a using a calibration method as described in U.S. patent application Ser. No. 15/548,138. The device fiducial marker 232a is depicted on the manipulator arm 210 but may also be positioned on the base 208 or the end-effector assembly 201. Registration algorithms may be executed to determine the POSE and coordinate transforms between a bone B, a tracking array 232c or 232d, and a surgical plan, using the registration methods described in U.S. Pat. Nos. 6,033,415, and 8,287,522.

Upon assembly of the device tracking array 232a to the surgical robot 202 prior to surgery, the POSE's of the coordinate systems, 232a and the end effector tool 203, are fixed relative to each other and stored in memory to accurately track the end effector tool 203 during the surgery (see for example U.S. Patent Publication 20140039517 A1) relative to the bone anatomy (e.g., bones B). The POSE data may be used by the computing system 204 during the procedure to update the bone and surgical plan coordinate transforms so the surgical robot 202 can accurately execute the surgical plan in the event any bone motion occurs. However, if there is unintentional movement between the tracking arrays (232c, 232d) and the bone B after initially registering the bone B, then the bone needs to be re-registered to re-establish the coordinate systems between the tracking arrays (232c, 232d) and the bone B, which may be accomplished with embodiments of the inventive method described herein. It should be appreciated that in certain embodiments, other tracking systems may be incorporated with the surgical system 200 such as an electromagnetic field tracking system or a 6-DOF mechanical tracking system. An example of a 6-DOF mechanical tracking system is described in U.S. Pat. No. 6,322,567. In a particular inventive embodiment, the surgical system 200 does not include a tracking system 206, but instead employs a bone fixation and monitoring system that fixes the bone directly to the surgical robot 202 and monitors bone movement as described in U.S. Pat. No. 5,086,401.

Other Embodiments

Patents and publications detailed herein are representative of the skill in art at the time of the present invention. These references are hereby incorporated by reference to the same extent as if each patent or publication was specifically and individually incorporated by reference.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A method for determining if hardware inserted in a bone is located at least partially within a cut volume of bone to be removed, comprising;
   registering the cut volume to a position of the bone;
   digitizing a first position and orientation (POSE) of a first piece of hardware inserted in the bone with a digitizer probe having a probe tip; and
   calculating, with a processor, if any portion of the first piece of hardware is located at least partially within the cut volume using the registered position of the cut volume; and the digitized POSE of the first piece of hardware.

2. The method of claim 1 wherein a location of the probe tip is determined by at least one of: an electro-mechanical sensor arm, an optical tracking system, an electro-magnetic tracking system, or an ultrasound tracking system.

3. The method of claim 1 wherein the calculation utilizes a point-distance algorithm, wherein a plurality of points is defined along a length of the first piece of hardware and the point-distance algorithm determines a distance or proximity of the cut volume relative to each point from the plurality of points.

4. The method of claim 1 wherein the hardware is inserted as part of a surgical procedure that is computer-assisted total joint replacement (TJR) surgery.

5. The method of claim 1 wherein the first piece of hardware comprises a recovery marker having a divot.

6. The method of claim 1 further comprising providing feedback regarding a location of the probe tip as a user navigates the probe tip along a surface of the bone to locate a position for inserting a second piece of hardware in the bone that is outside the cut volume.

7. The method of claim 6 wherein the feedback is in the form of a visual signal displayed on a monitor, an acoustic signal, or a haptic signal.

8. The method of claim 7 wherein the monitor displays a distance calculator.

9. The method of claim 1 wherein the first piece of hardware is at least one of a screw, a pin, a recovery marker, or a probe.

10. The method of claim 1 further comprising:
    digitizing a position and orientation (POSE) of a second piece of hardware installed in the bone; and calculating, with a processor, if any portion of the second piece of hardware is located inside or outside the cut volume using the registered position of the cut volume and the digitized POSE of the second piece of hardware.

11. The method of claim 1 wherein a tracking array is configured to couple to the first piece of hardware.

12. A system for determining if hardware inserted in a bone is located at least partially within a cut volume of bone to be removed comprising:
    a first piece of hardware to be installed in the bone;
    a digitizer probe comprising a probe tip;
    a computing system comprising a processor and memory, said memory storing the cut volume of bone to be removed from the bone, wherein the computing system is configured to: register the cut volume to a position of the bone; digitize a position and orientation (POSE) of the first piece of hardware installed in the bone; and calculate if any portion of the first piece of hardware is located at least partially within the cut volume using the registered position of the cut volume and the digitized POSE of the first piece of hardware.

13. The system of claim 12 wherein the computing system is further configured to:
    instruct a user to install a second piece of hardware in the bone if the first piece of hardware is inside the cut volume; and
    calculate if the second piece of hardware installed in the bone is located at least partially within the cut volume.

14. The system of claim 12 wherein the calculation utilizes a point-distance algorithm, wherein a plurality of points is defined along a length of the first piece of hardware and the point-distance algorithm determines a distance or proximity of the cut volume relative to each point from the plurality of points.

15. The method of claim 12 wherein the first piece of hardware is at least one of a screw, a pin, a recovery marker, or a probe.

* * * * *